United States Patent [19]

Thomas et al.

[11] 4,161,528
[45] Jul. 17, 1979

[54] 1,3-DIPHENYL-2-TRICHLOROMETHYL-IMIDAZOLIDINES

[75] Inventors: Klaus Thomas, Gau-Algesheim; Walter Ost, Bingen; Jurgen Curtze, Geisenheim-Johannisberg, all of Fed. Rep. of Germany

[73] Assignee: Celamerck GmbH & Co. KG., Ingelheim am Rhein, Fed. Rep. of Germany

[21] Appl. No.: 878,669

[22] Filed: Feb. 17, 1978

Related U.S. Application Data

[63] Continuation of Ser. No. 776,365, Mar. 10, 1977, abandoned, which is a continuation of Ser. No. 660,410, Feb. 23, 1976, abandoned, which is a continuation-in-part of Ser. No. 573,822, May 2, 1975, abandoned, which is a continuation-in-part of Ser. No. 427,368, Dec. 21, 1973, abandoned.

[30] Foreign Application Priority Data

Dec. 23, 1972 [DE] Fed. Rep. of Germany ....... 2263239
Feb. 28, 1975 [DE] Fed. Rep. of Germany ....... 2508715

[51] Int. Cl.² ................. C07D 233/10; A61K 31/395
[52] U.S. Cl. ................................. 424/273 R; 548/300
[58] Field of Search ...................... 548/300; 424/273 R

[56] References Cited

U.S. PATENT DOCUMENTS 3,197,478  7/1965  Wanzlick et al. ................. 260/309.7

FOREIGN PATENT DOCUMENTS 2263237  6/1974  Fed. Rep. of Germany.

OTHER PUBLICATIONS

Wanzlick et al. II Chem. Ber., 1961, vol. 94, pp. 2389-2393.
Wanzlick et al. III Chem. Ber., 1963, vol. 96, pp. 1208-1212.

*Primary Examiner*—Alan L. Rotman
*Attorney, Agent, or Firm*—Hammond & Littell

[57] ABSTRACT

Compounds of the formula

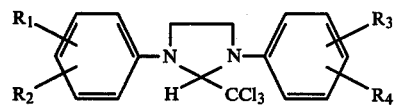

wherein
$R_1$ and $R_2$ are each hydrogen, halogen or lower alkyl, attached to the 3-, 4- or 5-positions of the phenyl ring,
$R_3$ is halogen, lower alkyl or lower alkoxy, attached to the 3- or 4-position of the phenyl ring, and
$R_4$ is hydrogen, halogen or lower alkyl, attached to the 4- or 5-position of the phenyl ring;

provided, however, that the two phenyl moieties are other than both 4-chloro- or 4-methyl-substituted at the same time; the compounds are useful as insecticides and acaricides.

7 Claims, No Drawings

1,3-DIPHENYL-2-TRICHLOROMETHYL-IMIDAZOLIDINES

This is a continuation of copending application Ser. No. 776,365 filed Mar. 10, 1977, now abandoned; which in turn is a continuation of copending application Ser. No. 660,410 filed Feb. 23, 1976, now abandoned; which in turn is a continuation-in-part of copending application Ser. No. 573,822 filed May 2, 1975, now abandoned; which in turn is a continuation-in-part of copending application Ser. No. 427,368 filed Dec. 21, 1973, now abandoned.

This invention relates to novel 1,3-diphenyl-2-trichloromethyl-imidazolidines and a method of preparing these compounds.

More particularly, the present invention relates to a novel class of imidazolidines represented by the formula

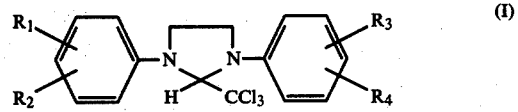

wherein
$R_1$ and $R_2$ are each hydrogen, halogen or lower alkyl, attached to the 3-, 4- or 5-positions of the phenyl ring,
$R_3$ is halogen, lower alkyl or lower alkoxy, attached to the 3- or 4-position of the phenyl ring, and
$R_4$ is hydrogen, halogen or lower alkyl, attached to the 4- or 5-position of the phenyl ring;
provided, however, that the two phenyl moieties are other than both 4-chloro- or 4-methyl-substituted at the same time when $R_1$ and $R_4$ are hydrogen.

A subgenus thereunder is constituted by compounds of the formula

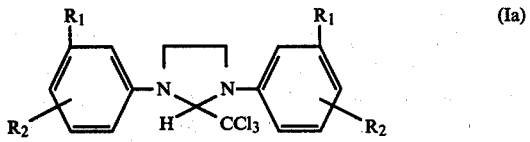

wherein
$R_1$ is halogen, lower alkyl or, when $R_2$ is 4-fluoro, 4-bromo, 4-iodo, 4-(lower alkyl of more than 1 carbon atom) or 4-(lower alkoxy of more than 1 carbon atom), also hydrogen, and
$R_2$ is attached to the 4- or 5-position of the phenyl ring and is hydrogen, halogen or lower alkyl.

A further subgenus thereunder is constituted by those compounds of the formula Ia wherein $R_1$ is halogen, methyl or ethyl, and $R_2$ is hydrogen, methyl or ethyl in the 4- or 5-position on the phenyl ring.

A still further subgenus thereunder is constituted by those compounds of the formula Ia wherein $R_1$ is chlorine, bromine or methyl, and $R_2$ is hydrogen, chlorine, bromine or methyl in 4- or 5-position of the phenyl ring.

The compounds embraced by formula I above may be prepared by known processes, such as that of H. W. Wanzlick et al, Berichte 94, 2839 (1961), that is, by subjecting an N,N'-diphenyl-ethylene diamine of the formula

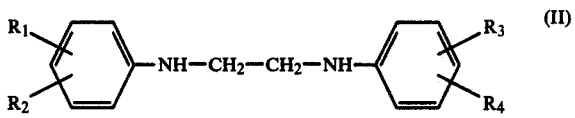

wherein $R_1$, $R_2$, $R_3$ and $R_4$ have the same meanings as in formula I, to a ring closure reaction with chloral.

This ring closure reaction has heretofore been carried out primarily with glacial acetic acid or a mixture of glacial acetic acid and hydrochloric acid as the solvent medium at room temperature or moderately elevated temperatures. However, in those instances where the phenyl moieties of the ethylenediamine derivative are 3-substituted or 3,5-disubstituted, as in formula Ia, the use of those solvent media produces no yield or very poor yields of the desired end product.

We have discovered that by performing the ring closure reaction in the presence of a water-immiscible or substantially water-immiscible solvent medium, such as benzene, toluene or xylene, and removing the water formed by the reaction by azeotropic distillation, significantly improved yields of all of the end products of the formula I, even of those where the phenyl moieties are p-substituted, are obtained. The reaction may be accelerated by the addition of a catalyst, such as p-toluenesulfonic acid.

The starting compounds of the formula II may be prepared by reacting a compound of the formula

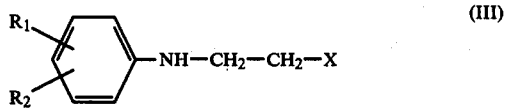

wherein
$R_1$ and $R_2$ have the same meanings as in formula I, and
X is an easily removable substituent such as chlorine or bromine,
with an aniline of the formula

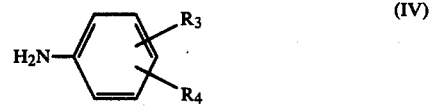

wherein $R_3$ and $R_4$ have the meanings previously defined, while splitting off HX. The compounds of the formula III are accessible by various methods, for example by reacting an aniline of the formula

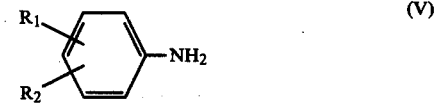

with ethyleneoxide [Houben-Weyl, Methoden der Organischen Chemie, Vol. XI/1, page 313 (1957)], or with ethylene chlorohydrin or ethylene bromohydrin, and thereafter replacing the hydroxyl group by group X, preferably by chlorine or bromine, according to conventional methods.

Some of the compounds of the formula III may also be obtained from a compound of the formula

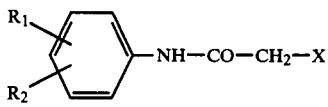

wherein $R_1$, $R_2$ and X have the meanings previously defined, by reduction with $NaAlH_2(OCH_2CH_2OCH_3)_2$ (Tetrahedron Letters 1968, page 3303).

The starting compounds for the preparation of the compounds embraced by the subgenus represented by formula Ia, that is, N,N'-diphenyl-ethylenediamines of the formula

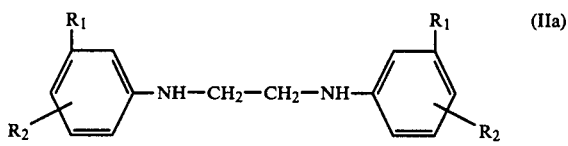

wherein $R_1$ and $R_2$ have the meanings previously defined, are also readily accessible by reacting a correspondingly substituted aniline with an ethylene dihalide [see H. W. Wanzlick et al, Berichte 86, 1463 (1953)]; or also by condensation with glyoxal analogous to J. M. Klieman et al, J. Org. Chem. 35, 3140 (1970).

The following examples illustrate the present invention and will enable others skilled in the art to understand it more completely. It should be understood, however, that the invention is not limited solely to the particular examples given below.

Preparation of starting compounds of the formula II

EXAMPLE A

N-(3-Chloro-phenyl)-N'-(4-methyl-phenyl)-ethylenediamine (a) N-(2-Hydroxy-ethyl)-3-chloro-aniline A mixture consisting of 50.8 gm of 3-chloro-aniline, 36 gm of ethylenechlorohydrin and 50 gm of anhydrous sodium carbonate was refluxed for four hours, while stirring. Thereafter, the reaction mixture was suction-filtered while still hot, and the filter cake was washed with ethyl acetate. The filtrate was then distilled in vacuo; the desired product passed over at 182° C./14 mm Hg.

(b) N-(2-Bromo-ethyl)-3-chloro-aniline hydrochloride 50 gm of 50% hydrobromic acid were slowly added dropwise to 19 gm of the product obtained in step (a), while stirring. The vessel containing the resulting mixture was then connected to a Vigreux-column, and the mixture was heated until a temperature of about 124° C. was reached. After three hours of heating at that temperature, about 35 ml of liquid were distilled off. The residue solidified upon cooling and was purified by washing with acetone, yielding 22 gm of the desired product which had a melting point of 148° C.

(c) A mixture consisting of 15.8 gm of N-(2-bromo-ethyl)-3-chloro-aniline hydrobromide, 10.7 gm of 4-methyl-aniline, 50 ml of toluene and 15 gm of anhydrous sodium carbonate was refluxed for eight hours, while stirring. Thereafter, the reaction mixture was filtered, the filter cake was washed with ethyl acetate, and the filtrate was evaporated in vacuo, leaving 10 gm of an oil which was used as the starting material in Example 11 without further purification. It was identified to be N-(3-chloro-phenyl)-N'-(4-methyl-phenyl)-ethylenediamine.

EXAMPLE B

N-Phenyl-N'-(3,5-dimethyl-phenyl)-ethylenediamine (a) [N-(3,5-Dimethyl-phenyl)-glycine]-anilide A mixture consisting of 17 gm of chloroacetanilide, 20 gm of 3,5-dimethyl-aniline and 15 gm of sodium carbonate was heated for six hours on an oil bath at 135° C. Thereafter, the reaction mixture was admixed with water, and the organic phase was taken up with ethyl acetate. The organic solution was dried over sodium sulfate and then evaporated in vacuo, leaving 20 gm of a light-brown oil which gradually solidified.

(b) The product obtained in step (a) was dissolved in 35 ml of benzene, and the resulting solution was added dropwise to a solution of 35 gm of sodium bis-(2-methoxy-ethoxy)-dihydroaluminate in 100 ml of benzene. The temperature of the resulting mixture rose spontaneously, and hydrogen was given off. The mixture was refluxed for two hours, allowed to cool, and then 200 ml of aqueous 20% sulfuric acid were added dropwise thereto. Subsequently, the solution was purged of benzene with steam, and the aqueous residue was made alkaline with concentrated ammonia and then diluted to 2 liters with water. The aqueous mixture was now extracted with ethyl acetate, and the organic extract solution was evaporated in vacuo, leaving the desired product as an oil which was used as the starting material in Example 12 without further purification.

The starting compounds of the formula II for Examples 13–23 were prepared in analogous manner.

Preparation of end products of the formula I

EXAMPLE 1

1,3-Bis-(3'-chloro-phenyl)-2-trichloromethyl-imidazolidine (a) A mixture consisting of 188 gm of ethylene bromide, 383 gm of 3-chloro-aniline and 300 gm of sodium carbonate was stirred at 140° C. for five hours. Thereafter, the reaction mixture was cooled to about 80° C., and by addition of water the inorganic substances were caused to go into solution. The mixture was then extracted with ethyl acetate, the organic extract was dried over sodium sulfate, and the solvent as well as unreacted 3-chloroaniline were distilled off in vacuo, leaving 205 gm (76% of theory) of raw N,N'-bis-(3-chloro-phenyl)-ethylenediamine. The raw product may be purified by distillation at 16 mm Hg and about 285° C.

(b) A mixture consisting of 112.4 gm of the raw product obtained in (a), 500 ml of benzene, 100 gm of chloral and 10 gm of p-toluene sulfonic acid was heated for six hours in a vessel equipped with a water trap. Thereafter, the reaction solution was concentrated as much as possible by evaporation in vacuo, and the residue was taken up in 100 ml of glacial acetic acid while warming. Upon cooling of the solution, a crystalline product separated out which was collected by vacuum filtration, washed first with a little cold glacial acetic acid and then with ice-cold methanol, and dried, yielding 115 gm (70% of theory) of the compound of the formula

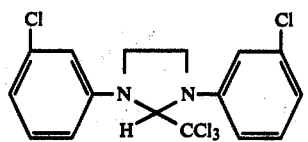

which had a melting point of 90° C.

EXAMPLE 2

Using a procedure analogous to that described in Example 1b, 1,3-bis-(m-tolyl)-2-trichloromethyl-imidazolidine, m.p. 132° C., was prepared from N,N'-bis-(m-tolyl)-ethylenediamine and chloral.

EXAMPLE 3

Using a procedure analogous to that described in Example 1b, 1,3-bis-(p-fluoro-phenyl)-2-trichloromethylimidazolidine, m.p. 119° C., was prepared from N,N'-bis-(p-fluoro-phenyl)-ethylenediamine and chloral.

EXAMPLE 4

Using a procedure analogous to that described in Example 1b, 1,3-bis-(p-bromo-phenyl)-2-trichloromethylimidazolidine, m.p. 164° C., was prepared from N,N'-bis-(p-bromo-phenyl)-ethylenediamine and chloral.

EXAMPLE 5

Using a procedure analogous to that described in Example 1b, 1,3-bis-(p-iodo-phenyl)-2-trichloromethylimidazolidine, m.p. 172° C., was prepared from N,N'-bis-(p-iodo-phenyl)-ethylenediamine and chloral.

EXAMPLE 6

Using a procedure analogous to that described in Example 1b, 1,3-bis-(3',4'-xylyl)-2-trichloromethyl-imidazolidine, m.p. 120° C., of the formula

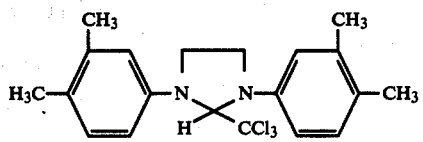

was prepared from N,N'-bis-(3',4'-xylyl)-ethylenediamine and chloral.

EXAMPLE 7

Using a procedure analogous to that described in Example 1b, 1,3-bis-(3',5'-dichloro-phenyl)-2-trichloromethyl-imidazolidine, m.p. 197° C., of the formula

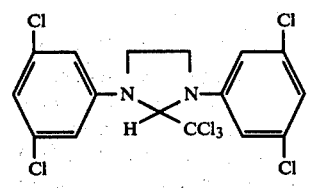

was prepared from N,N'-bis-(3',5'-dichloro-phenyl)-ethylenediamine and chloral.

EXAMPLE 8

Using a procedure analogous to that described in Example 1b, 1,3-bis-(3',5'-dimethyl-phenyl)-2-trichloromethyl-imidazolidine, m.p. 152° C., was prepared from N,N'-bis-(3',5'-dimethyl-phenyl)-ethylenediamine and chloral.

EXAMPLE 9

Using a procedure analogous to that described in Example 1b, 1,3-bis-(3'-chloro-4'-fluoro-phenyl)-2-trichloromethyl-imidazolidine, m.p. 105° C., was prepared from N,N'-bis-(3'-chloro-4'-fluoro-phenyl)-ethylene diamine and chloral.

EXAMPLE 10

Using a procedure analogous to that described in Example 1b, 1,3-bis-(3'-bromo-4'-methyl-phenyl)-2-trichloromethyl-imidazolidine, m.p. 167° C., of the formula

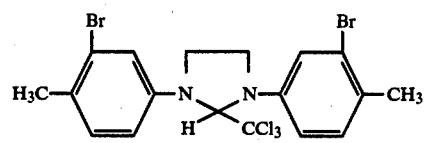

was prepared from N,N'-bis-(3'-bromo-4'-methyl-phenyl)-ethylenediamine and chloral.

EXAMPLE 11

1-(3-Chloro-phenyl)-3-(4-methyl-phenyl)-2-trichloromethyl-imidazolidine

A mixture consisting of 12.2 gm of N-(3-chloro-phenyl)-N'-(4-methyl-phenyl)-ethylenediamine, 9 gm of chloral, 100 ml of toluene and 1.2 gm of p-toluenesulfonic acid was heated at its boiling point for 45 minutes in a vessel equipped with a water trap. Thereafter, the reaction mixture was filtered while still hot, and the filtrate was evaporated in vacuo. The oily residue was allowed to cool and was then triturated with a little glacial acetic acid, whereupon crystallization occurred. The crystals were collected by suction filtration, washed with cold methanol, and recrystallized from ethanol, yielding 6.5 gm of the compound of the formula

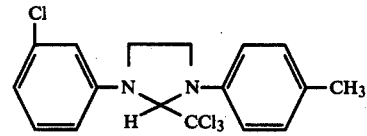

which had a melting point of 34°–36° C.

EXAMPLE 12

Using a procedure analogous to that described in Example 11, 1-phenyl-3-(3,5-dimethyl-phenyl)-2-trichloromethyl-imidazolidine, m.p. 130° C., was prepared from N-phenyl-N'-(3,5-dimethyl-phenyl)-ethylenediamine and chloral.

EXAMPLE 13

Using a procedure analogous to that described in Example 11, 1-phenyl-3-(4-methyl-phenyl)-2-trichloromethyl-imidazolidine, m.p. 80° C., was prepared from N-phenyl-N'-(4-methyl-phenyl)-ethylenediamine and chloral.

EXAMPLE 14

Using a procedure analogous to that described in Example 11, 1-phenyl-3-(4-methoxy-phenyl)-2-trichloromethyl-imidazolidine, m.p. 120°–122° C., was prepared from N-phenyl-N'-(4-methoxy-phenyl)-ethylenediamine and chloral.

EXAMPLE 15

Using a procedure analogous to that described in Example 11, 1-phenyl-3-(4-chloro-phenyl)-2-trichloromethyl-imidazolidine, m.p. 141°–144° C., was prepared from N-phenyl-N'-(4-chloro-phenyl)-ethylenediamine and chloral.

EXAMPLE 16

Using a procedure analogous to that described in Example 11, 1-(3-chloro-phenyl)-3-(4-chloro-phenyl)-2-trichloromethyl-imidazolidine, m.p. 138° C., was prepared from N-(3-chloro-phenyl)-N'-(4-chloro-phenyl)-ethylenediamine and chloral.

EXAMPLE 17

Using a procedure analogous to that described in Example 11, 1-(4-methyl-phenyl)-3-(4-methoxy-phenyl)-2-trichloromethyl-imidazolidine, m.p. 111°–113° C., was prepared from N-(4-methyl-phenyl)-N'-(4-methoxy-phenyl)-ethylenediamine and chloral.

EXAMPLE 18

Using a procedure analogous to that described in Example 11, 1-(4-methyl-phenyl)-3-(4-chloro-phenyl)-2-trichloromethyl-imidazolidine, m.p. 124°–125° C., was prepared from N-(4-methyl-phenyl)-N'-(4-chloro-phenyl)-ethylenediamine and chloral.

EXAMPLE 19

Using a procedure analogous to that described in Example 11, 1-(4-methyl-phenyl)-3-(4-ethyl-phenyl)-2-trichloromethyl-imidazolidine, m.p. 98°–100° C., was prepared from N-(4-methyl-phenyl)-N'-(4-ethyl-phenyl)-ethylenediamine and chloral.

EXAMPLE 20

Using a procedure analogous to that described in Example 11, 1-(3-methyl-phenyl)-3-(3-chloro-phenyl)-2-trichloromethyl-imidazolidine, an oil, was prepared from N-(3-methyl-phenyl)-N'-(3-chloro-phenyl)-ethylenediamine and chloral.

EXAMPLE 21

Using a procedure analogous to that described in Example 11, 1-(3,5-dichloro-phenyl)-3-(3,5-dimethyl-phenyl)-2-trichloromethyl-imidazolidine, m.p. 163° C., was prepared from N-(3,5-dichloro-phenyl)-N'-(3,5-dimethyl-phenyl)-ethylenediamine and chloral.

EXAMPLE 22

Using a procedure analogous to that described in Example 11, 1-(3,5-dimethyl-phenyl)-3-(4-chloro-phenyl)-2-trichloromethyl-imidazolidine, m.p. 112° C., was prepared from N-(3,5-dimethyl-phenyl)-N'-(4-chloro-phenyl)-ethylenediamine and chloral.

EXAMPLE 23

Using a procedure analogous to that described in Example 11, 1-(4-methyl-phenyl)-3-(3,5-dichloro-phenyl)-2-trichloromethyl-imidazolidine, m.p. 117° C., was prepared from N-(4-methyl-phenyl)-N'-(3,5-dichloro-phenyl)-ethylenediamine and chloral.

The compounds embraced by formula I above have useful properties. More particularly, they exhibit insecticidal and acaricidal activities. Even at relatively low concentrations, they effectively kill flies (e.g. *Musca domestica*), roaches (e.g. *Phyllodroma germanica*), spider mites (e.g. *Tetranychus urticae*), aphids (e.g. *Aphis fabae*), caterpillars (e.g. of *Plutella maculipennis*) and bugs (e.g. *Epilachna varivestis*).

Since the compounds of this invention are selective in their insecticidal and acaricidal action, they are well suited for specific plant protection; moreover, they are practically non-toxic toward warm-blooded animals. Particularly of interest is the fact that, in agricultural use, the compounds very rapidly degrade into harmless compounds while giving off chloroform and thus are ecologically acceptable.

For insecticidal and acaricidal purposes the compounds of the present invention are incorporated as active ingredients into conventional agricultural pesticidal compositions, that is, compositions consisting essentially of an inert liquid or solid carrier and an effective amount of the active ingredient, such as aerosols, emulsion concentrates, wettable powders, dusting powders, granulates or colloidal forms.

The effective concentration range of the active ingredient in these compositions is from 0.02 to 5% by weight, based on the total weight. In the case of concentrates, such as emulsion concentrates, wettable powders and the like, this effective concentration range is achieved by diluting the concentrated composition containing up to 30% by weight of active ingredient with the required amount of water prior to use.

The following examples illustrate a few insecticidal and acaricidal compositions comprising a compound of the present invention as an active ingredient and represent the best modes contemplated of putting the invention into practical use. The parts are parts by weight unless otherwise specified.

EXAMPLE 24

Wettable powder

The powder is compounded from the following ingredients:

| | | |
|---|---|---|
| 1,3-Bis-(m-tolyl)-2-trichloromethyl-imidazolidine | 50 | parts |
| Sodium lignin sulfonate | 8 | " |
| Sodium naphthalene sulfonate | 2 | " |
| Kaolin | 20 | " |
| Silicious chalk | 20 | " |

Preparation:

The ingredients are admixed with each other, and the mixture is milled in a stud mill to a particle size of about 2 to 6 μ. Prior to use, the resulting powder is admixed with the required amount of water to make a sprayable suspension containing from about 0.02 to 5% by weight of the imidazolidine compound, depending upon the strength desired.

The active ingredient content may be raised to 80 parts with a corresponding reduction in the amount of the inert carrier ingredients.

EXAMPLE 25

Dusting powder

The powder is compounded from the following ingredients:

| | | |
|---|---:|---|
| 1-Phenyl-3-(4-chloro-phenyl)-2-trichloromethyl-imidazolidine | 1.5 | parts |
| Talcum | 90.0 | " |
| Aluminum stearate | 0.5 | " |

Preparation:

The imidazolidine compound is milled in a stud mill, and the resulting powder is homogeneously admixed with the other compounds.

EXAMPLE 26

Colloid formulation

The composition is compounded from the following ingredients:

| | | |
|---|---:|---|
| 1,3-Bis-(m-tolyl)-2-trichloromethyl-imidazolidine | 20.0 | parts |
| Ethoxylated isotridecanol polyglycol ether (wetting agent, emulsifier) | 2.5 | " |
| Ethoxylated coconut fatty alcohol polyglycol ether (wetting agent, emulsifier) | 2.5 | " |
| Alkylphenol polyglycol ether | 1.5 | " |
| Liquid n-paraffins | 73.5 | " |

Preparation:

The ingredients are pre-dispersed, and the dispersion is then milled in a glass bead mill to a particle size under 2 µ, 20% under 1.1 µ.

EXAMPLE 27

Aerosol spray

The spray composition is compounded from the following ingredients:

| | | |
|---|---:|---|
| 1-(3-Chloro-phenyl)-3-(p-tolyl)-2-trichloromethyl-imidazolidine | 0.5 | parts |
| Talcum | 35.0 | " |
| Zinc stearate | 0.5 | " |
| Hexadecyl alcohol | 0.5 | " |
| Propellant (e.g. frigens) | 63.5 | " |

Preparation:

The ingredients, except the propellant, are admixed, the mixture is filled into aerosol cans, and the cans are pressurized with the propellant in conventional manner.

Propane/butane, nitrogen, carbon dioxide or air may also be used as propellants.

Any one of the other imidazolidine compounds embraced by formula I may be substituted for the particular imidazolidine compound in Examples 24 to 27. Likewise, the amount of active ingredient in these illustrative examples may be varied to achieve the concentration range set forth above, and the amounts and nature of the inert carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

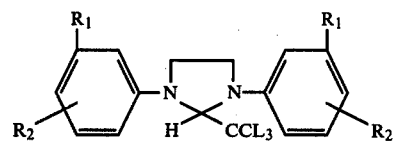

wherein
   $R_1$ is halogen, lower alkyl or, when $R_2$ is 4-fluoro, 4-bromo, 4-iodo or 4-(lower alkyl of more than 1 carbon atom), also hydrogen; and
   $R_2$ is attached to the 4- or 5-position of the phenyl ring and is hydrogen, halogen or lower alkyl.

2. A compound of claim 1,
where
   $R_1$ is halogen, methyl or ethyl; and
   $R_2$ is hydrogen, methyl or ethyl.

3. A compound of claim 1,
where
   $R_1$ is chlorine, bromine or methyl, and
   $R_2$ is hydrogen, chlorine, bromine or methyl.

4. The compound of claim 1, which is 1,3-bis-(3'-chloro-phenyl)-2-trichloromethyl-imidazolidine.

5. The compound of claim 1, which is 1,3-bis-(3',5'-dimethyl-phenyl)-2-trichloromethyl-imidazolidine.

6. An insecticidal and acaricidal composition consisting essentially of an inert solid or liquid carrier and from about 0.02 to 80% by weight, based on the total weight, of a compound of claim 1.

7. The method of killing insects and acarids, which comprises contacting said insects and acarids with an insecticidally and acaricidally effective amount of a compound of claim 1.

* * * * *